(12) United States Patent
House

(10) Patent No.: US 8,728,057 B2
(45) Date of Patent: May 20, 2014

(54) DEVICES AND METHODS FOR CATHETER ADVANCEMENT

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 95 days.

(21) Appl. No.: 12/793,993

(22) Filed: Jun. 4, 2010

(65) Prior Publication Data

US 2010/0312227 A1 Dec. 9, 2010

Related U.S. Application Data

(60) Provisional application No. 61/184,265, filed on Jun. 4, 2009.

(51) Int. Cl.
*A61M 27/00* (2006.01)

(52) U.S. Cl.
USPC .................................................. 604/544

(58) Field of Classification Search
USPC .................................................. 604/544
See application file for complete search history.

(56) References Cited

U.S. PATENT DOCUMENTS

| | | | | |
|---|---|---|---|---|
| 3,556,294 A * | 1/1971 | Walck et al. | ........ | 206/210 |
| 3,766,915 A * | 10/1973 | Rychlik | ........ | 604/161 |
| 3,794,042 A * | 2/1974 | De Klotz et al. | ........ | 604/523 |
| 4,062,363 A * | 12/1977 | Bonner, Jr. | ........ | 604/171 |
| 4,311,139 A * | 1/1982 | Smith | ........ | 604/28 |
| 4,342,313 A * | 8/1982 | Chittenden | ........ | 604/159 |
| 4,713,057 A * | 12/1987 | Huttner et al. | ........ | 604/164.07 |
| 5,176,647 A * | 1/1993 | Knoepfler | ........ | 604/158 |
| 5,376,094 A * | 12/1994 | Kline | ........ | 606/113 |
| 5,843,002 A * | 12/1998 | Pecor et al. | ........ | 600/585 |
| 6,004,305 A * | 12/1999 | Hursman et al. | ........ | 604/328 |
| 6,036,707 A * | 3/2000 | Spaulding | ........ | 606/159 |
| 6,050,976 A * | 4/2000 | Thorne et al. | ........ | 604/164.01 |
| 6,053,905 A * | 4/2000 | Daignault et al. | ........ | 604/544 |
| 6,077,244 A * | 6/2000 | Botich et al. | ........ | 604/110 |
| 6,090,075 A * | 7/2000 | House | ........ | 604/172 |
| 6,213,978 B1 * | 4/2001 | Voyten | ........ | 604/164.01 |
| 6,355,004 B1 * | 3/2002 | Pedersen et al. | ........ | 600/581 |
| 6,475,189 B1 * | 11/2002 | Lilley, Jr. | ........ | 604/164.01 |
| 6,942,652 B1 * | 9/2005 | Pressly et al. | ........ | 604/508 |
| 7,189,223 B2 * | 3/2007 | Kear | ........ | 606/1 |
| 7,255,685 B2 * | 8/2007 | Pressly et al. | ........ | 604/164.08 |
| 7,500,965 B2 * | 3/2009 | Menzi et al. | ........ | 604/198 |
| 7,632,256 B2 * | 12/2009 | Mosler et al. | ........ | 604/349 |
| 2002/0032436 A1 * | 3/2002 | Mogg | ........ | 606/1 |
| 2004/0147923 A1 * | 7/2004 | Kear | ........ | 606/47 |
| 2007/0213734 A1 * | 9/2007 | Bleich et al. | ........ | 606/79 |

(Continued)

*Primary Examiner* — Susan Su
*Assistant Examiner* — Guy K Townsend
(74) *Attorney, Agent, or Firm* — Moazzam & Associates, LLC

(57) ABSTRACT

Catheter advancing devices, systems and methods for advancing a catheter into the urethra of a user are disclosed. The catheter advancement device includes a body portion that couples to a guide portion of the catheter, the guide portion being movably coupled to the proximal end of a catheter. The catheter advancement device further includes a pair of flexible handles extending outwards from the body portion, and a gripping portion extending inwards from each of the flexible handles. A surface of the gripping portion comes in contact with the catheter when the flexible handles are engaged, and the surface of the gripping portion in contact with the catheter applies pressure to the catheter when the handles are engaged to advance the catheter through the guide portion.

18 Claims, 6 Drawing Sheets

(56) References Cited

U.S. PATENT DOCUMENTS

| | | | |
|---|---|---|---|
| 2008/0097362 A1* | 4/2008 | Mosler et al. | 604/349 |
| 2009/0043287 A1* | 2/2009 | Mosler et al. | 604/544 |
| 2009/0137986 A1* | 5/2009 | Golden et al. | 604/544 |
| 2009/0306591 A1* | 12/2009 | Amisar et al. | 604/122 |

* cited by examiner

US 8,728,057 B2

DEVICES AND METHODS FOR CATHETER ADVANCEMENT

This U.S. Utility Patent Application claims priority to U.S. Provisional Patent Application Ser. No. 61/184,265, filed Jun. 4, 2009, the content of which is hereby incorporated by reference in its entirety into this disclosure.

BACKGROUND OF THE INVENTION

1. Field of the Invention

The present invention relates to urinary catheters. More specifically, the present invention relates to the advancement of a catheter by a person with limited manual dexterity.

2. Background of the Invention

Intermittent catheterization of an individual's urinary bladder is a common practice today for many persons who are in a hospital setting, a nursing home, doctor's office, rehabilitation facility or at home. For instance, a patient is sometimes catheterized to treat such conditions as urinary retention, the inability to evacuate urine, or for the purpose of obtaining a sterile urine specimen from a patient in a doctor's office or at home.

The need for intermittent catheterization of an individual sometimes arises due to problems typically associated with long term use of indwelling catheters, such as infections, urethral damage, and bladder damage. Long term use of an indwelling catheter is also a risk factor for bladder cancer. This is often the case for persons having a neurogenic urinary condition (neurogenic bladder), such as in a spinal cord injury, multiple sclerosis, stroke, or brain injury. Conditions that interfere with the individual's ability to voluntarily void the bladder may also arise post-surgically or as a result of benign prostatic hypertrophy, prostate cancer or diabetes mellitus.

Many of the affected individuals are capable of, and would prefer to perform self-catheterization. For many, the level of risk and discomfort of repeated catheterizations carried out over the course of a day (at 3-6 hour intervals, for example) are offset by the accompanying convenience, privacy or self-reliance that is achieved. Some of the major difficulties that arise in self-catheterization are the lack of satisfactory catheterization kits, the problem of maintaining the required level of sanitation during the procedure, and the difficulty of sometimes performing the procedure under conditions of restricted space and privacy. In assisted or non-self-catheterizations, it is common practice in hospitals to employ a catheterization tray, which typically includes a sterile drape, gloves, a conventional catheter, antiseptic solution, swabs, lubricant, forceps, underpad and a urine collection container. Assisted catheterization is usually performed with the patient in a supine position. Maintaining a sterile field during the procedure can still be a problem, however, and the "cath tray" procedure is impractical for use with some individuals and situations today.

Many individuals with spinal cord injuries or other neurological diseases routinely perform intermittent catheterization several times a day using conventional catheters or kits and "clean technique." Clean technique means that the urethral area is initially wiped with a moist soapy washcloth, and efforts are made to avoid contamination of the catheter during the procedure. The user's hands are not sterile and a sterile field is not maintained. Clean technique is used instead of sterile technique, generally, for two reasons. First, it is very difficult, if not impossible, for individuals who are performing self-catheterization to adhere strictly to sterile technique. Secondly, these individuals are required to catheterize themselves between 3 and 6 times a day, and the cost of a new sterile catheter and the accessories required to perform sterile catheterization become excessively expensive for many users. Sometimes an individual will reuse a "cleaned" catheter. As a result, the use of non-sterile technique will many times result in contamination and subsequent infection of the urinary tract, causing significant morbidity and cost to the patient and society.

Even if cost considerations were not a major consideration for the user, with most conventional self-contained sterile units where the collection bag doubles as the catheter insertion cover, the catheter is extremely difficult for the user to grasp and insert. This is particularly a problem for self-catheterization users who may also have neurological problems that limit manual dexterity. Also, with some of the available catheter kits and methods, the catheter is either not sufficiently lubricated during insertion (and thus requires the additional application of possibly non-sterile lubricant), or the catheter is too slick with lubricant and cannot effectively be grasped through an insufficiently flexible bag. As a practical matter, most individuals who would prefer to self-catheterize cannot conveniently do so, and maintain the required level of sanitation using many of the existing catheterization apparatus.

Spinal cord injuries at the C5, C6, or C7 level affect the use of a person's hands and make these tasks difficult or impossible with current products. However, people who have had strokes, brain injuries, or multiple sclerosis may also require catheterization but have limited dexterity. The current catheterization market does not currently support the needs of these people.

Many catheterization tasks require a degree of dexterity to accomplish. People with normal dexterity, like paraplegics, may not have use of their lower extremities, but their hands are normal. Quadriplegics can have use of their upper extremities, having absolutely normal movement, like a paraplegic, except for normal hand dexterity. Thus, many tasks requiring a degree of hand dexterity are very difficult for paraplegics to accomplish.

Insertion of a catheter is one such task. With limited dexterity, even if an individual can insert the tip of the catheter, applying steady pressure to insert the remainder of the catheter can be difficult. What is therefore needed is a device or method to allow a person with limited dexterity to advance a catheter into the urethra.

SUMMARY OF THE INVENTION

The present invention solves the problems described above using a catheter advancement device attached to or bundled with a catheter. The catheter advancement device comprises a body portion that couples to a guide portion of the catheter, the guide portion being movably coupled to the proximal end of a catheter. The catheter advancement device further comprises a pair of flexible handles extending outwards from the body portion, and a gripping portion extending inwards from each of the flexible handles. A surface of the gripping portion comes in contact with the catheter when the flexible handles are engaged. The surface of the gripping portion in contact with the catheter applies pressure to the catheter when the handles are engaged. The pressure advances the catheter through the guide portion.

The catheter advancement device further comprises an elbow portion coupled to the gripping portion, the elbow portion having a textured surface that comes in contact with the catheter when the flexible handles are engaged. The pressure applied to the catheter by the gripping portion may be adjustable to prevent damage to the bladder while still maintaining efficacy. The catheter advancement device further comprises a membrane coupled to a lubricant reservoir of the guide portion, the membrane preventing the catheter from slipping backwards when the flexible handles are released.

In one exemplary embodiment, the present invention is a catheter advancement device. The catheter advancement device includes a body portion adapted to be coupled to a guide portion of a catheter, the guide portion being movably coupled to the catheter, a pair of flexible handles extending outwards from the body portion in a direction away from the guide portion, and a flexible gripping member extending from an inner surface of each of the pair of flexible handles in a direction towards the guide portion, each flexible gripping member being of a smaller length than the corresponding flexible handle. A gripping surface of the gripping member comes in contact with the catheter when the flexible handles are engaged, and applies pressure to the catheter, the pressure advancing the catheter in a direction towards the guide portion.

In another exemplary embodiment, the present invention is a catheter assembly. The catheter assembly includes a catheter having a proximal end, a distal end, and a sheath, a guide portion coupled to the sheath and surrounding the proximal end of the catheter, and a catheter advancement device. The catheter advancement device includes a body portion coupled to the guide portion, a pair of flexible handles extending outwards from the body portion, and a flexible gripping member extending inwards from each of the pair of flexible handles, the flexible gripping members providing a friction with the catheter and sheath. Engagement of the flexible handles causes the flexible gripping members to advance the catheter through the guide portion.

In yet another exemplary embodiment, the present invention is a catheter assembly including a catheter having a proximal end and a distal end, and a catheter advancement device including a body portion coupled to a guide tip, a pair of flexible handles extending outwards from the body portion, and a flexible gripping member extending inwards from each of the pair of flexible handles, the flexible gripping members providing a friction with the catheter. The body portion is 360° circumferential and wraps entirely around the catheter, and engagement of the flexible handles causes the flexible gripping members to advance the catheter through the guide tip of the body portion

DETAILED DESCRIPTION OF THE INVENTION

Figure 1:
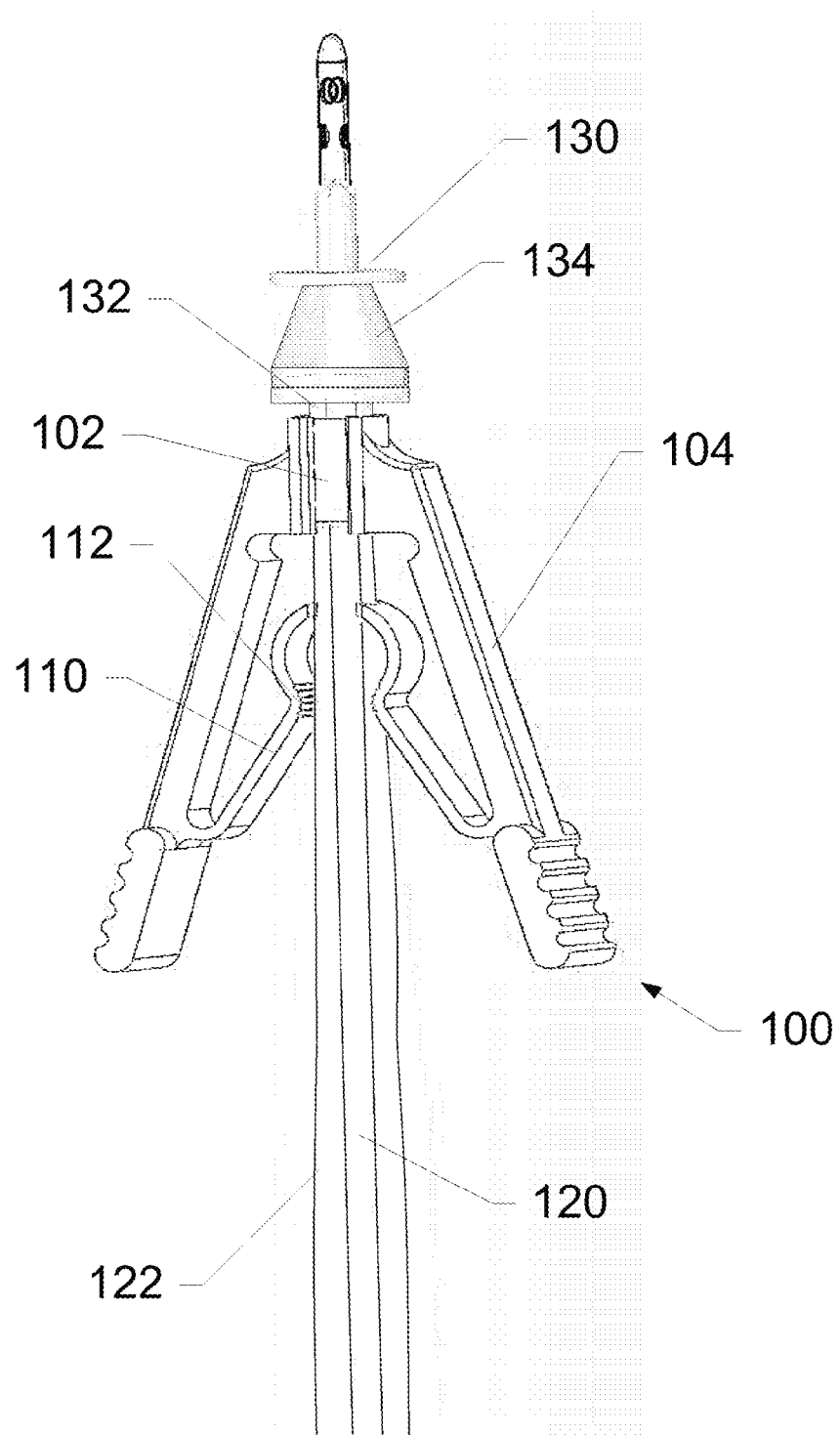
FIG. 1 shows a catheter advancement device coupled to a catheter, according to an exemplary embodiment of the present invention.

The present invention provides a catheter advancing device for advancing a catheter into the urethra of a user. The catheter advancement device comprises a body portion that couples to a guide portion of the catheter, the guide portion being movably coupled to the catheter. The guide initially encloses a proximal end, or tip, of the catheter. The catheter advancement device further comprises a pair of flexible handles extending outwards from the body portion, and a gripping portion extending inwards from each of the flexible handles. A surface of the gripping portion comes in contact with the catheter when the flexible handles are engaged, and the surface of the gripping portion in contact with the catheter applies pressure to the catheter when the handles are engaged to advance the catheter through the guide portion. The rate of advancement and the pressure applied can be controlled by a user with limited dexterity, simply by adjusting the user's grip on the flexible handles.

The catheter advancement device further comprises an elbow portion coupled to the gripping portion, the elbow portion having a textured surface that comes in contact with the catheter when the flexible handles are engaged. The pressure applied to the catheter by the gripping portion may be adjustable to prevent damage to the bladder while still maintaining efficacy. The catheter advancement device further comprises a membrane coupled to the reservoir of the guide portion, the membrane preventing the catheter from slipping backwards when the flexible handles are released.

The present application refers to subject matter described in commonly-owned U.S. Pat. No. 6,090,075 (the '075 patent), issued on Jul. 18, 2000, the contents of which are fully and entirely incorporated by herein by reference. Briefly, a urinary catheterization system includes a catheter having a proximal end (tip) and a distal end. The distal end is coupled to a fluid collection bag. The catheter may be enclosed in a sheath. The proximal end of the catheter is coupled to a guide tip, or guide portion. Other elements may be incorporated into the catheter, and are described in the '075 patent.

With regard to the instant invention, a catheter advancement device is attached, either removably or permanently, to the guide portion of the catheter. The catheter advancement device includes a body portion that is coupled to the guide portion, a pair of flexible handles extending outward from the body portion, and a gripping member extending inwards from an inner surface of each one of the pair of flexible handles. The gripping members have a tip that is textured such that it creates friction when coming into contact with the catheter. When the flexible handles are engaged, the gripping member grips and advances the catheter through the guide portion.

Near the proximal end of the catheter described in the '075 patent is a membrane or diaphragm situated between the interior space of the catheter and a lubrication reservoir of the guide portion. The membrane holds lubricant inside the lubrication reservoir until it is needed for lubricating the tip and the outside surface of the catheter. This membrane also serves to prevent the catheter from slipping backwards while the flexible handles are in a released state. The membrane may be made of silicon or any other material capable of performing this function.

The catheterization process begins with a user partially inserting the proximal end, or tip of the catheter into the urethra. The guide portion may also have a tip that is partially insertable into the urethra to provide for stable insertion of the catheter. The user then squeezes or engages the flexible handles, which include gripping portions extending inwards towards the catheter. Squeezing the handles inwards causes the gripping portions to apply pressure on the portion of the catheter away from the urethra, bringing the catheter towards the guide portion, thereby advancing the catheter further into the urethra through the guide portion. When the flexible handles are released, the gripping portions lose contact with the catheter and resume their original position, while the membrane prevents the catheter from sliding back through the guide portion. The user squeezes the flexible handles again, advancing another portion of the catheter toward the guide portion and into the urethra. This process can be repeated until the catheter is fully inserted. Further, a user with limited or absent dexterity can simply use one hand to compress the flexible handles.

A release mechanism is implemented, such that the pressure applied by the gripping portions does not damage the bladder. In one embodiment, the pressure applied to the catheter is adjusted so that it is enough to advance the catheter, but not so strong that it drives through the bladder itself. The pressure can be adjusted by varying a coefficient of friction between the catheter and the gripping portions, by selecting a surface material or padded surface that has an optimal coefficient of friction, etc. In embodiments where the catheter is surrounded by a sheath, the materials of the gripping surface and the sheath are selected so that the bladder does not get damaged due to excessive force. A curved portion that curves around the diameter of the catheter can be coupled to each gripping portion. The curved portion retains the sheath material between the body portion and the curved portion.

In exemplary embodiments of the present invention, the body portion of the catheter advancement device is detachable from the guide portion. This allows the catheter advancement device to be removed from one catheter and attached to different catheters that are designed for individuals having differing levels of dexterity.

For the following description, it can be assumed that most correspondingly labeled structures across the figures (e.g., 132 and 232, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1 shows a catheter advancement device 100 coupled to a catheter 120, according to an exemplary embodiment of the present invention. Catheter advancement device 100 is used to advance catheter 120 through a guide portion 130 into the urethra of a user. Catheter advancement device 100 couples to a collar 132 of guide portion 130 of catheter 120. Specifically, body portion 102 of catheter advancement device 100 is fixedly or removably coupled around collar 132. The coupling may occur around collar 132 below a lubricant reservoir 134 of guide portion 130. Flexible gripping portions 110 extend from an inner surface of each of the pair of flexible handles 104 in a direction towards guide portion 130. Each gripping portion 110 has a textured surface portion 112 that provides an amount of friction between surface 112 and either catheter 120 or a sheath 122 enclosing catheter 120.

To catheterize oneself, a user places guide portion 130 in the proper position such that the proximal end of catheter 120 is aligned for entry into the urethra. The user squeezes together flexible handles 104 of catheter advancement device 100. The engagement of flexible handles 104 causes flexible gripping portions 110 of catheter advancement device 100 to grip and apply pressure to catheter 120 towards the guide portion 130. This motion advances the proximal end or tip of catheter 120 into the urethra. Gripping portions 110 further serve to retract sheath 122 from catheter 120. The user then releases flexible handles 104 and re-applies pressure to flexible handles 104 to repeat this advancing motion of catheter 120. This process is repeated until catheter 120 is in fluid communication with the bladder of the user.

A membrane in lubricant reservoir 134 prevents catheter 120 from slipping back from guide portion 130 during the release of flexible handles 104. Flexible gripping portions 110 are constructed such that they apply an appropriate amount of advancement force to catheter 120 without applying enough force to puncture the bladder of the user. This may be accomplished by creating flexible gripping portions 110 of a material at a thickness that provides failure of the material before the bladder is punctured. Because flexible handles 104 must simply be squeezed inward, flexible handles 104 do not require dexterity for their use and may be engaged by fingers, fingertips, fists, arms, etc.

In embodiments of the invention, the catheter advancement device is coupled to the catheter when received by a user. This coupling may be permanent or removable. This embodiment is especially useful to users with limited manual dexterity, as the user is not required to manually couple the catheter advancement device to the catheter. In other embodiments of the invention, a catheter advancement device is received by a user who owns a plurality of catheters. The catheter advancement device may be coupled to each catheter to use the catheter and then decoupled from the catheter such that it may be used again on the next catheter.

Figure 2:
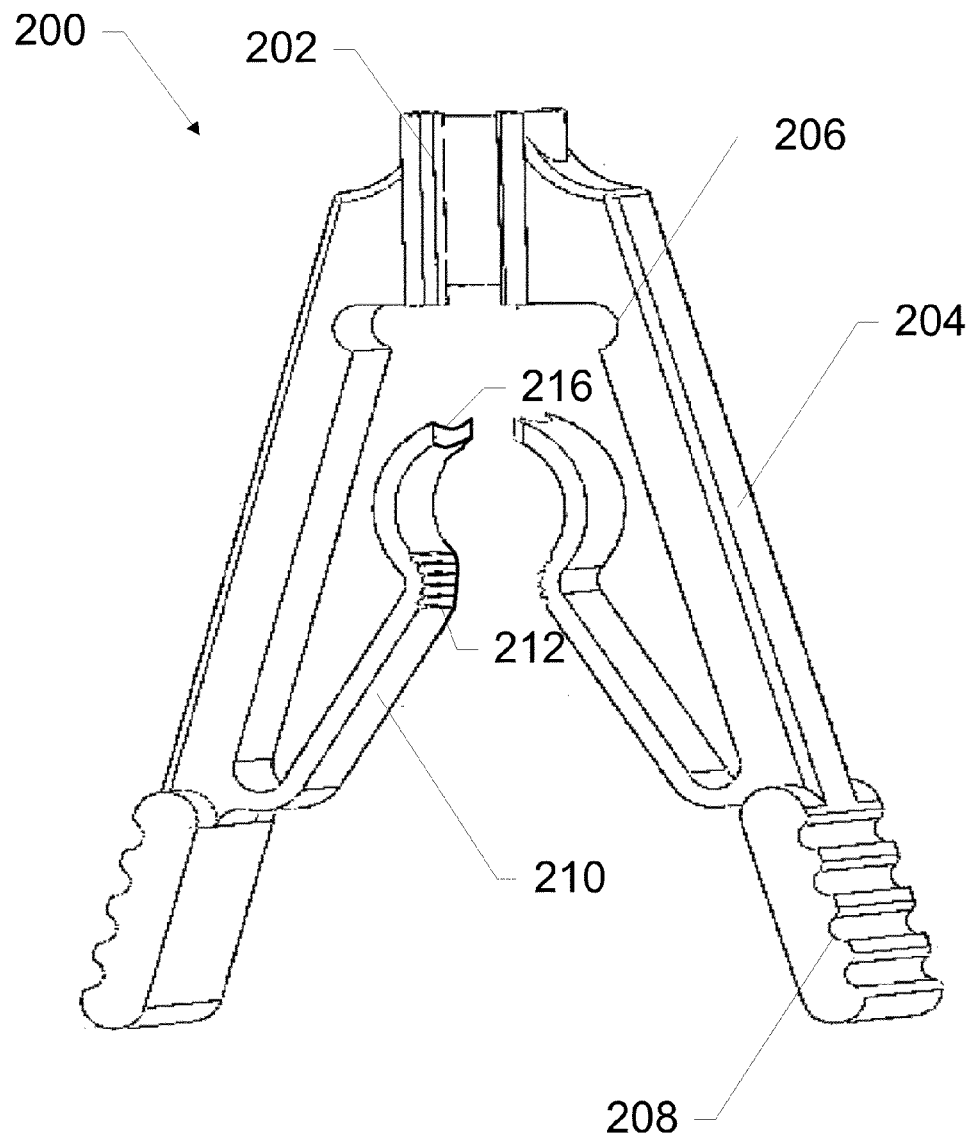
FIG. 2 shows a catheter advancement device, according to an exemplary embodiment of the present invention.

FIG. 2 shows a catheter advancement device 200, according to an exemplary embodiment of the present invention. In this embodiment, catheter advancement device 200 includes a body portion 202, flexible handles 204, hinge points 206, flexible gripping members 210, and curved portions 216. Body portion 202 is adapted to be coupled to a collar of a guide portion of a catheter. Body portion 202 securely fits around the collar with body portion 202 adapted to fit around any ridges of the collar to prevent slipping. Flexible handles 204 extend radially outwards from body portion 202 in a direction away from the position of the guide portion. Flexible handles 204 are coupled to body portion 202 via hinge points 206. Hinge points 206 are generally thinner than the rest of flexible handles 204. Thus, when pressure is applied to flexible handles 204, flexible handles 204 generally pivot about hinge point 206, as hinge point 206 is easier to bend. Hinge point 206 may not be necessary for certain materials, as the flexibility of the material may be sufficient. Flexible handles 204 include a textured or gripping portion 208 near the end of each of flexible handles 204. Gripping portion 208 prevents a user's fingers from slipping while using catheter advancement device 200. Flexible gripping members 210 extend from an inner surface of each of flexible handles 204 in a direction towards the guide portion of a secured catheter. Each of flexible gripping members 210 is a shorter length than the corresponding flexible handle 204. When flexible handles 204 are engaged, a gripping surface 212 of flexible gripping members 210 comes in contact with the catheter. Gripping surface 212 in contact with the catheter applies pressure to the catheter when flexible handles 204 are engaged, the pressure advancing the catheter in a direction towards the guide portion. Flexible gripping members 210 further have a curved portion 216 coupled to their ends. Curved portions 216 form an opening around the catheter, the opening being sized slightly larger than the outer diameter of the catheter. This provides room for any excess sheath material that may accumulate or "bunch" behind flexible gripping members 210 when flexible handles 204 are engaged and the catheter is being inserted.

Catheter advancement device 200 may be constructed of a single molded material or may be constructed of parts consisting of different materials. In embodiments of the invention, catheter advancement device 200 is constructed of a plastic material, such as polyvinylchloride (PVC). Gripping portion 208 may be molded into the material of catheter advancement device 200 or may be a separate material coupled to the end of each of flexible handles 204. For example, catheter advancement device 200 may be constructed of molded PVC while gripping portion 208 may be constructed of rubber. Gripping surface 212 may contain ridges that are angled such that the catheter is gripped and advanced through the guide portion when flexible handles 204 are engaged, but slides back along catheter without gripping catheter when flexible handles 204 are released. This prevents catheter from being pulled out by the release of flexible handles 204. Alternatively or additionally, catheter advancement device 200 or the guide portion of the catheter may contain a membrane that prevents the catheter from being pulled back by flexible gripping members 210. Gripping surface 212 may contain ridges that are angled such that the catheter is gripped and advanced through the guide portion when flexible handles 204 are engaged, but slides back along catheter without gripping catheter when flexible handles 204 are released. This prevents catheter from being pulled out by the release of flexible handles 204. Alternatively or additionally, catheter advancement device 200 or the guide portion of the catheter may contain a membrane that prevents the catheter from being pulled back by flexible gripping members 210.

Figure 3:
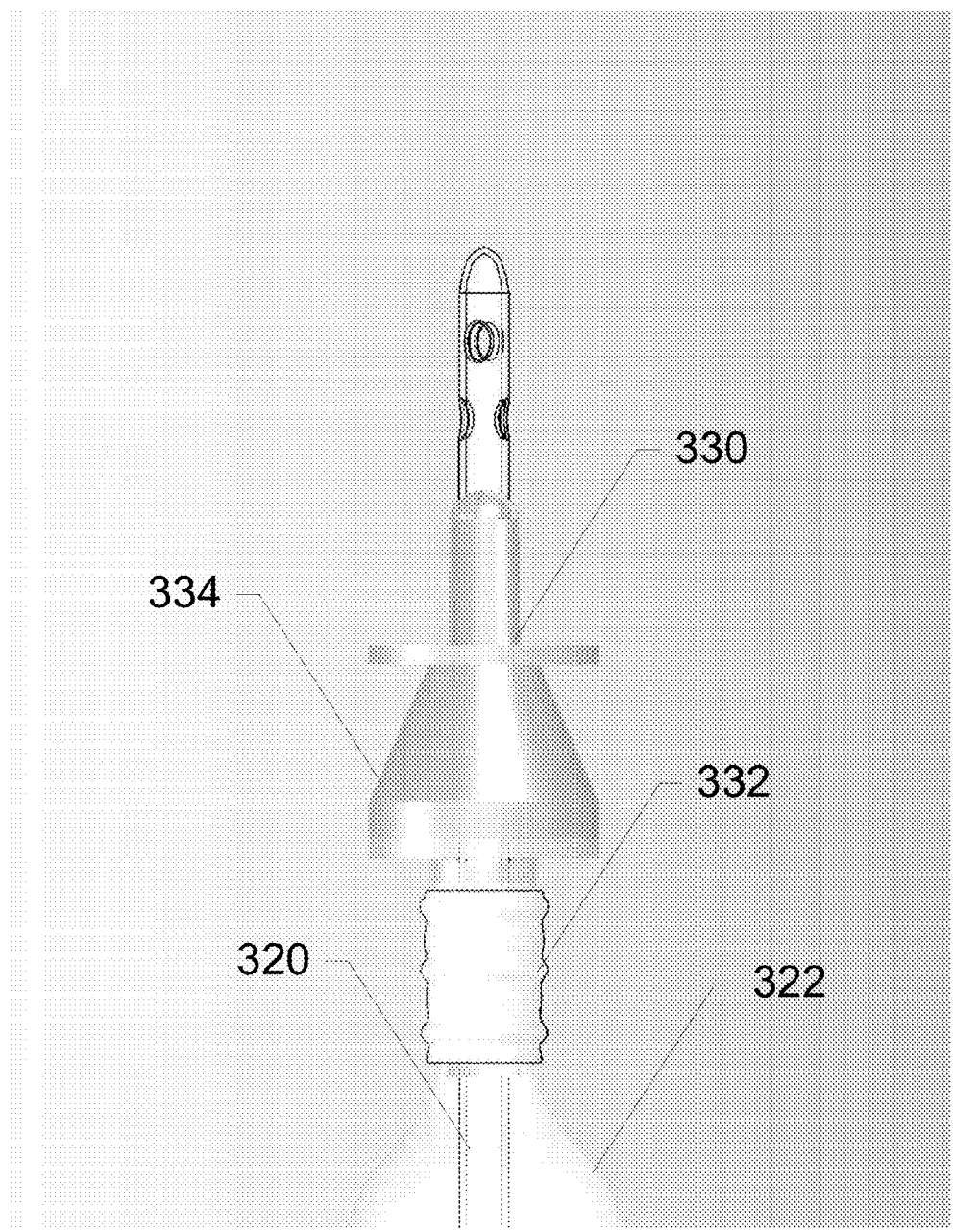
FIG. 3 shows a catheter including a guide portion, according to an exemplary embodiment of the present invention.

FIG. 3 shows a catheter 320 including a guide portion 330, according to an exemplary embodiment of the present invention. Catheter 320 is a catheter such as that in the '075 patent. In this embodiment, guide portion 330 includes a collar 332 where a sheath 322 attaches to guide portion 330 and a lubricant reservoir 334. Collar 332 also provides an attachment point for a catheter advancement device. Collar 332 is constructed of a fairly rigid material, such that a catheter advancement device may secure around guide portion 330, and such that the portion of the catheter directly behind lubricant reservoir 332 does not collapse under the forward pressure of the catheter advancement device. Collar 332 may contain ridges, etc., such that a coupling between collar 332 and the catheter advancement device is secure. Lubricant reservoir 334 stores a lubricant to lubricate catheter 320 as catheter 320 advances through guide portion 330. Lubricant reservoir 334 includes a membrane that prevents the lubricant from leaking out of lubricant reservoir 334 and prevents catheter 320 from slipping backwards through guide portion 330. This may be accomplished by the membrane causing friction when catheter 320 retracts. During catheterization, catheter 320 is advanced through guide portion 330 and into a user's urethra.

Figure 4:
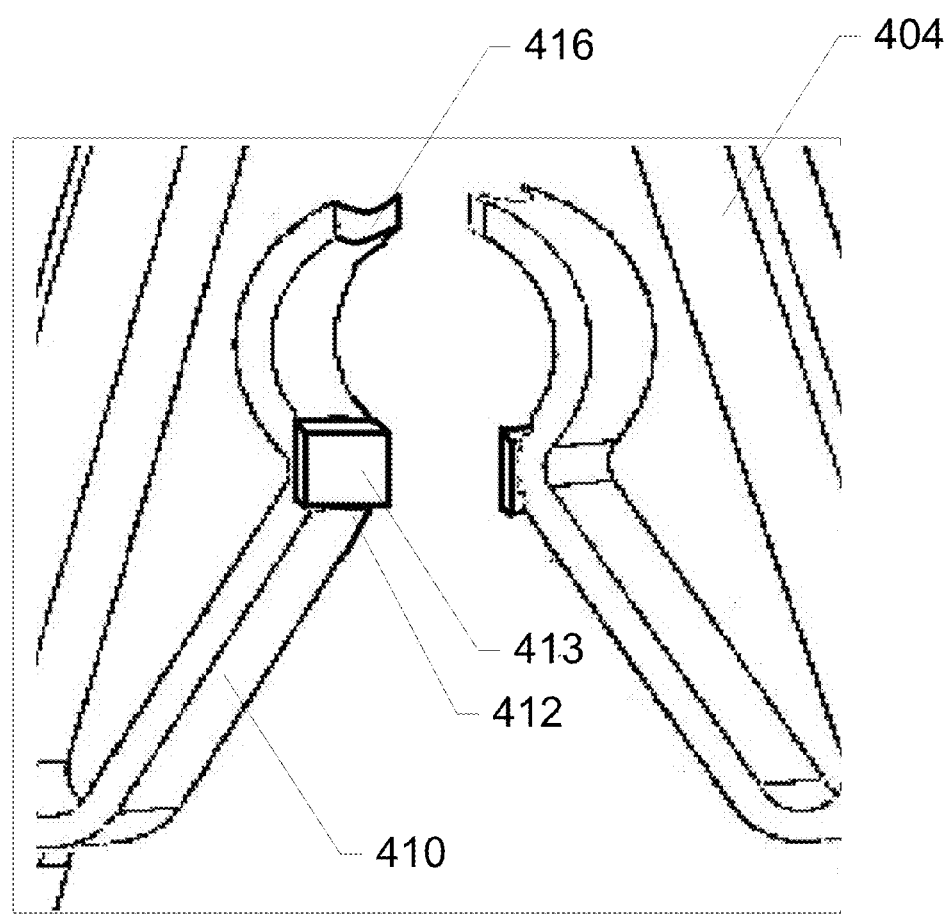
FIG. 4 shows flexible gripping portions of a catheter advancement device, according to an exemplary embodiment of the present invention.

FIG. 4 shows flexible gripping portions 410 of a catheter advancement device, according to an exemplary embodiment of the present invention. In this embodiment of the present invention, flexible gripping portions 410 include a padded surface 413 at a gripping surface 412 to protect a catheter as the catheter is being advanced. Padded surface 413 allows flexible gripping portions 410 to provide pressure to advance the catheter without damaging the catheter or a sheath surrounding the catheter. Padded surface 413 may be constructed of a relatively soft material, such as felt or a foam material. Flexible gripping members 410 further have a curved portion 416 coupled to them, wherein curved portion 416 forms an opening around the distal end of the catheter. This provides room for the excess sheath material that may accumulate or "bunch" behind flexible gripping members 410 when flexible handles 404 are engaged and the catheter is being inserted.

Figure 5:
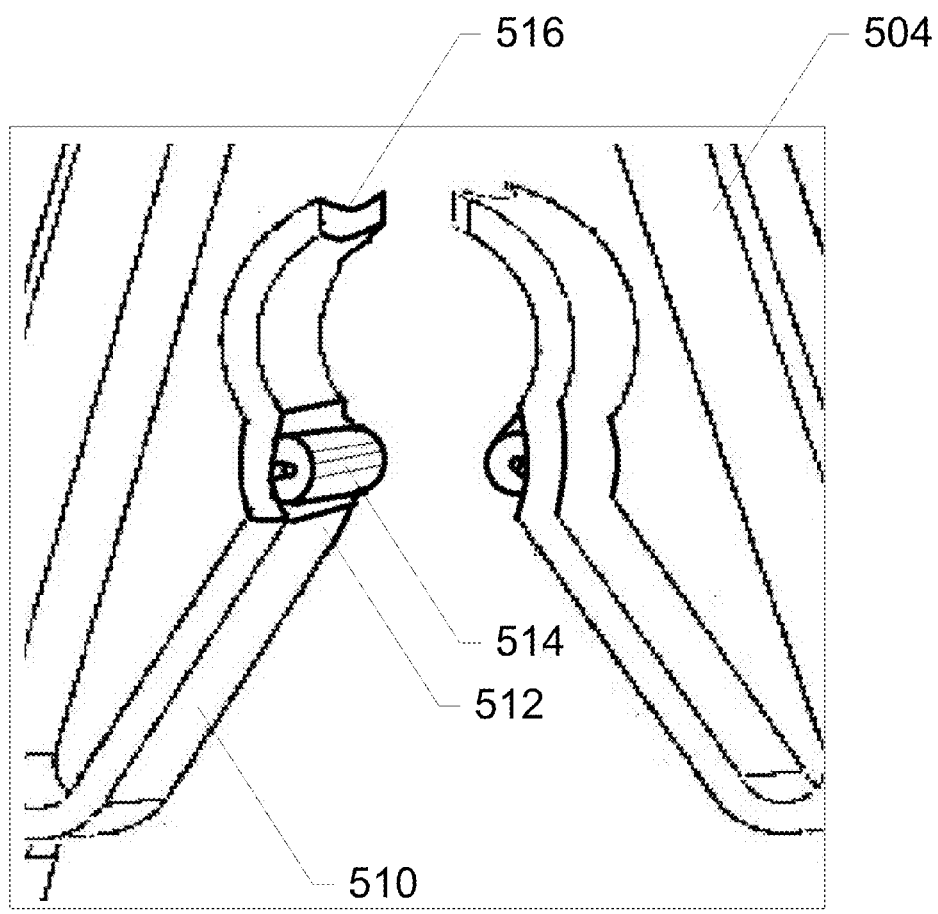
FIG. 5 shows flexible gripping portions of a catheter advancement device, according to an exemplary embodiment of the present invention.

FIG. 5 shows flexible gripping portions 510 of a catheter advancement device, according to an exemplary embodiment of the present invention. In this embodiment of the present invention, flexible gripping portions 510 include a roller mechanism 514 at a gripping surface 512. Roller mechanism 514 serves to advance a catheter through a guide portion while preventing damage to the catheter or a sheath surrounding the catheter. Roller mechanism 514 provides pressure to the catheter when flexible handles 504 of catheter advancement device are engaged. When flexible handles 504 are released, roller mechanism 514 may roll back over catheter without pulling catheter out of the urethra of a user. Roller mechanism 514 may be constructed such that roller mechanism 514 only rolls one way, such that roller mechanism 514 does not roll as the catheter is being advanced, but rolls back over the catheter when flexible handles 504 are released. Alternatively, roller mechanism 514 is in a locked state while pressure is being applied, and unlocks when the handles are released. In either case, the rollers enable steady advancement of the catheter without causing damage to the surface of the catheter or sheath.

In some cases, it is beneficial to have a catheter assembly without a sheath and corresponding guide portion. This could be in the case of one-time use or hydrophilic catheters that can be slippery and difficult to handle. In such cases, a sterile catheter advancement device can be incorporated with the sheath-less catheter and optionally disposed of upon a successful catheterization.

Figure 6:
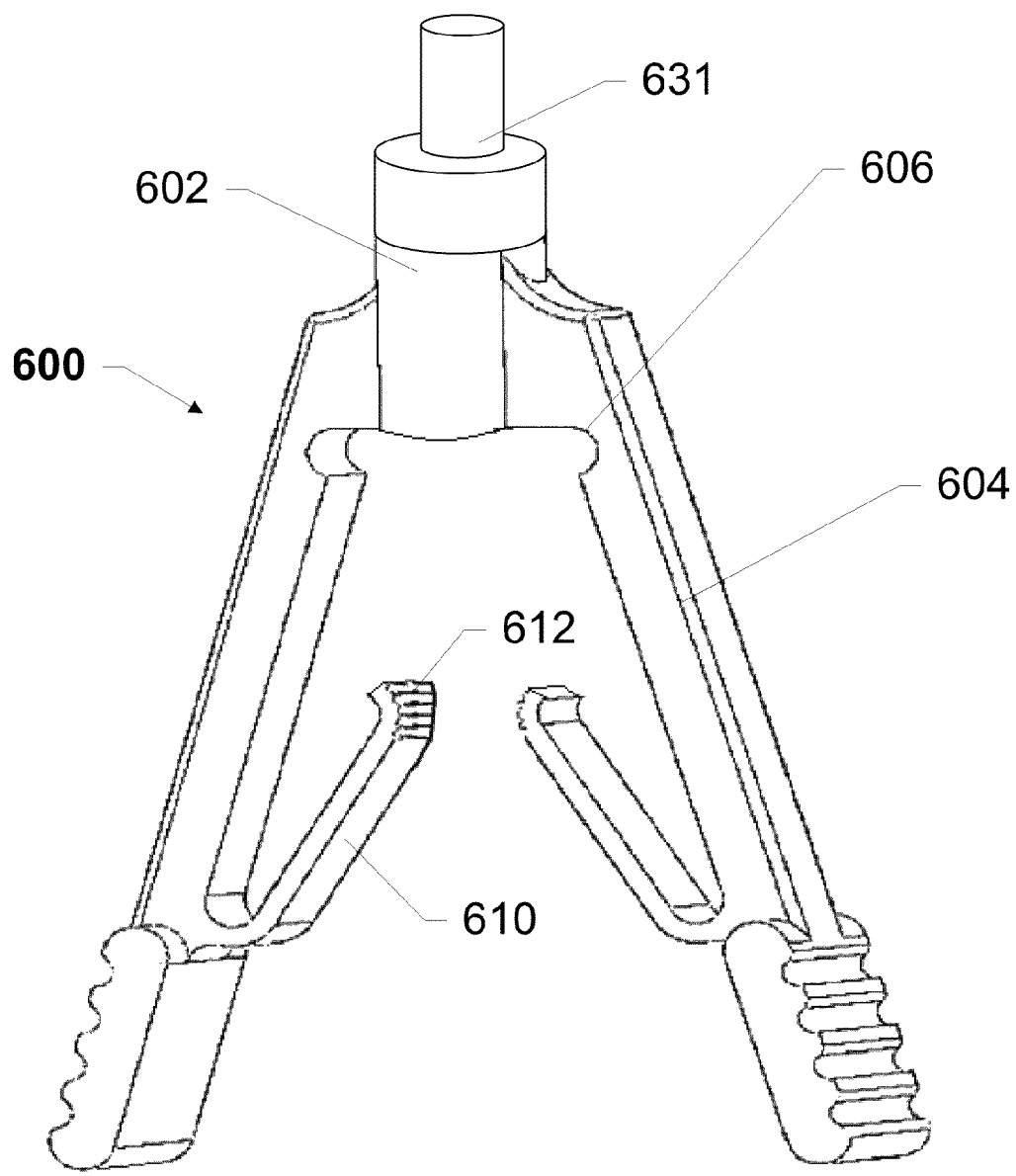
FIG. 6 shows a catheter advancement device including a guiding body portion, according to an exemplary embodiment of the present invention.

FIG. 6 shows a catheter advancement device including a guiding body portion, according to an exemplary embodiment of the present invention. In this embodiment, catheter advancement device 600 includes a body portion 602 that is 360° circumferential. This means that body portion 602 wraps entirely around a catheter, instead of being clamped onto a guide portion or removably coupled to a guide portion. Moreover, body portion 602 is fixedly coupled to a guide tip 631. Although catheter advancement device 600 has the same hinge portion 606, flexible handles 604, and flexible gripping members 610, the flexible gripping members 610 terminate with flexible surface 612. Notably, there is no need for curved portions to retain a sheath, since this embodiment is for use with catheters having no sheaths. In use, a catheter is gripped by gripping members 610, advances through body portion 602 and through guide tip 631, and enters the urethra. The user can position guide tip 631 to partially enter the urethra for optimal catheterization. Sterile catheter advancement device 600 can be disposed of, or can be cleaned for reuse.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A catheter advancement device, comprising:
a body portion adapted to be coupled to a guide portion of a catheter, the guide portion being movably coupled to the catheter;
a pair of flexible handles extending outwards from the body portion in a direction away from the guide portion;
a flexible gripping member extending from an inner surface of each of the pair of flexible handles in a direction towards the guide portion, each flexible gripping member being of a smaller length than the corresponding flexible handle; and
a curved portion coupled to an end of each flexible gripping member, the curved portion forming an opening sized to fit around an outer diameter of the catheter when the flexible handles are engaged, the curved portion for retaining excess sheath material;
wherein a gripping surface of the flexible gripping member comes in contact with the catheter when the flexible handles are engaged and applies pressure to the catheter, such that engaging the flexible handles causes the flexible gripping members to advance the catheter through the guide portion.

2. The catheter advancement device of claim 1, wherein the guide portion includes a collar, the collar providing a coupling point for the catheter advancement device.

3. The catheter advancement device of claim 1, wherein the gripping surface has a padded surface.

4. The catheter advancement device of claim 3, wherein the padded surface is a felt pad.

5. The catheter advancement device of claim 1, wherein the gripping surface comprises a rolling mechanism, the rolling mechanism being in a locked state when the flexible handles are engaged.

6. The catheter advancement device of claim 1, wherein the flexible handles include a hinge point, the hinge point being a location on each flexible handle about which the flexible handle pivots.

7. The catheter advancement device of claim 1, wherein the gripping surface includes a plurality of ridges angled towards the guide portion, the plurality of ridges providing friction to the catheter when the flexible handles are engaged and sliding back along the catheter with relatively less friction when the flexible handles are released.

8. The catheter advancement device of claim 1, further comprising a membrane coupled to the guide portion, the membrane preventing the catheter from slipping backwards when the flexible handles are released.

9. A catheter assembly, comprising:
a catheter having a proximal end, a distal end, and a sheath;
a guide portion coupled to the sheath and surrounding the proximal end of the catheter; and
a catheter advancement device including a body portion coupled to the guide portion, a pair of flexible handles extending outwards from the body portion, and a flexible gripping member extending inwards from each of the pair of flexible handles, the flexible gripping members providing a friction with the catheter and the sheath, and a curved portion coupled to an end of each flexible gripping member, the curved portion forming an opening sized to fit around an outer diameter of the catheter when the flexible handles are engaged, the curved portion for retaining excess sheath material;
wherein engagement of the flexible handles causes the flexible gripping members to advance the catheter through the guide portion.

10. The catheter assembly of claim 9, further comprising a collar coupled to the guide portion, the collar providing a coupling point for the catheter advancement device.

11. The catheter assembly of claim 9, further comprising a lubricant reservoir including a membrane, the membrane preventing a lubricant from exiting the lubricant reservoir towards the catheter advancement device.

12. The catheter assembly of claim 11, wherein the membrane further prevents the catheter from slipping backwards through the guide portion when the flexible handles are released.

13. The catheter assembly of claim 9, wherein the gripping surface has a padded surface.

14. The catheter assembly of claim 13, wherein the padded surface is a felt pad.

15. The catheter assembly of claim 9, wherein the gripping surface comprises a rolling mechanism, the rolling mechanism being in a locked state when the flexible handles are engaged.

16. The catheter assembly of claim 9, wherein the flexible handles include a hinge point, the hinge point being a location on each flexible handle about which the flexible handle pivots.

17. The catheter assembly of claim 9, wherein the gripping surface includes a plurality of ridges angled towards the guide portion, the plurality of ridges providing friction to the catheter when the flexible handles are engaged and sliding back along the catheter with relatively less friction when the flexible handles are released.

18. A catheter assembly, comprising:
a catheter having a proximal end and a distal end; and
a catheter advancement device including a body portion coupled to a guide tip, a pair of flexible handles extending outwards from the body portion, and a flexible gripping member extending inwards from each of the pair of flexible handles, the flexible gripping members providing a friction with the catheter, a curved portion coupled to an end of each flexible gripping member, the curved portion forming an opening sized to fit around an outer diameter of the catheter when the flexible handles are engaged, the curved portion for retaining excess sheath material;
wherein the body portion is 360° circumferential and wraps entirely around the catheter, and
wherein engagement of the flexible handles causes the flexible gripping members to advance the catheter through the guide tip of the body portion.

* * * * *